United States Patent [19]

Chase et al.

[11] Patent Number: 5,318,361
[45] Date of Patent: Jun. 7, 1994

[54] RAPID TEMPERATURE CYCLING FOR ACCELERATED STRESS TESTING

[75] Inventors: Eugene W. Chase; Francis DeRosa, both of Middletown; Michael P. Dugan, Toms River; Burton A. Unger, Monmouth Beach, all of N.J.

[73] Assignee: Bell Communications Research, Inc., Livingston, N.J.

[21] Appl. No.: 71,425

[22] Filed: Jun. 1, 1993

[51] Int. Cl.$^5$ .................... G01N 25/00; G01N 25/72; G01N 3/60; G01N 17/00
[52] U.S. Cl. .......................... 374/57; 62/3.3; 73/865.6
[58] Field of Search ............. 374/57; 73/865.6; 62/3.3, 125

[56] References Cited

U.S. PATENT DOCUMENTS

| | | | |
|---|---|---|---|
| H229 | 3/1987 | Phillips | 73/865.6 |
| 2,915,898 | 12/1959 | Van Luik, Jr. | 73/77 |
| 3,084,454 | 4/1963 | Schueller | 73/865.6 |
| 4,729,246 | 3/1988 | Melgaard et al. | 374/57 |
| 4,782,664 | 11/1988 | Sterna et al. | 62/3.3 |
| 4,787,752 | 11/1988 | Fraser et al. | 374/57 |
| 4,848,090 | 7/1989 | Peters | 62/3.3 |
| 4,854,726 | 8/1989 | Lesley et al. | 374/57 |
| 4,989,626 | 2/1991 | Takagi et al. | 62/3.3 |
| 4,995,273 | 2/1991 | Kisima et al. | 374/57 |
| 5,039,228 | 8/1991 | Chalmers | 374/57 |

FOREIGN PATENT DOCUMENTS

| | | | |
|---|---|---|---|
| 3217906 | 11/1983 | Fed. Rep. of Germany | 62/3.3 |
| 0223533 | 10/1986 | Japan | 374/57 |
| 403158740 | 7/1991 | Japan | 374/57 |
| 403248035 | 11/1991 | Japan | 374/57 |
| 1251043 | 8/1986 | U.S.S.R. | 73/865.16 |
| 1714465 | 2/1992 | U.S.S.R. | 73/865.6 |

OTHER PUBLICATIONS

Gunn, J. et al., "Highly Accelerated Temperature and Humidity Stress Test Technique (HAST)", Reliability Physics 19th Annual Proceedings, Orlando, Fla., (Apr. 7–9, 1981), 1981 IEEE/IRPS, pp. 48–51.

Thermal Shock, MIL-STD-883C, Notice 12, Method 1011.9, Paragraph 3.1, Jul. 27, 1990, pp. 1–3.

Primary Examiner—Diego F. F. Gutierrez
Attorney, Agent, or Firm—Leonard Charles Suchyta; James W. Falk

[57] ABSTRACT

An environmental testing chamber (10) and thermal cycling method in which, in addition to stressing the device (20) under test with electrical bias (32), elevated temperature (12), pressure (16), and humidity (18) while the device is being monitored (32), a thermoelectric heat pump (26) quickly cycles the temperature of the device by pumping heat from the heat sink (22) mounting the device to another larger heat sink (24).

12 Claims, 2 Drawing Sheets

RAPID TEMPERATURE CYCLING FOR ACCELERATED STRESS TESTING

FIELD OF THE INVENTION

The invention relates generally to accelerated testing of equipment, such as electronic or opto-electronic integrated circuits. In particular, the invention relates to such testing that rapidly cycles temperatures.

BACKGROUND OF THE INVENTION

Reliability engineering attempts, at a minimum, to quantify failure rates of a particular type of component or system and to identify the failure mechanism involved. Since most failure mechanisms are not a priori known, reliability engineering must at a minimum experimentally measure the lifetime to failure of the part. Thereafter, it is desirable to identify why it failed and attempt to eliminate the failure mechanism from the equipment.

The local-exchange telephone industry imposes aggressive lifetime requirements on most of its hardware, on the order of several decades. It is obviously of little use to insert the part into a normal working environment and wait for such periods of time for a failure to occur in order to first identify the failure rate or mechanism. Accordingly, electronic components and even systems are often stressed at higher temperatures than ambient or operational temperature with the hope of accelerating a weakness or flaw that will cause the component or system to fail before it is shipped to the customer. This type of accelerated testing will only be successful if the failure mode is accelerated by increasing the temperature, which is not unusual since most failure modes involve a thermally activated process. If the part is simply left in an inoperative state at the elevated temperature and thereafter tested, the test is called a static or storage accelerated test.

On the other hand, if a part is used in an electrical circuit, a more realistic test activates or otherwise electrically stresses the part with a voltage while the part remains at an elevated temperature. This combined test is called a temperature-bias (TB) test.

If the parts may be used in a severe environment, such as high humidity, then the high temperature, electrical bias, and humidity are combined in one stressing oven or chamber to further accelerate failure. Such temperature-humidity-bias (THB) testing has shown that the combination of heat and humidity degrade components that are not sealed in an environmentally secure, i.e., hermetic package that does not allow the ambient atmosphere to penetrate to the active or most sensitive portion of the device being tested.

Often, a manufacturer will package electronic components in non-hermetic packages, such as a plastic epoxy packages, for a variety of reasons ranging from cost saving to improved high-frequency performance. A controversy remains about the validity of correlating THB testing to the typical environment that a component experiences. A number of experimenters have tried to extrapolate THB data to TB data or to ambient conditions. The correlation is important because, if correctly done, it would allow the manufacturer or customer of a part that is specified for a lifetime of, say, 25 years to know the performance of the part over that extended period.

Investigators have created even more harsh environments by adding yet another variable to THB testing, specifically, elevated pressure. Elevated pressure tests are particularly applicable to non-hermetic packages. Components are inserted into a pressure vessel or pressure cooker where they experience temperature, humidity, pressure, and electrical bias. At higher than normal atmospheric pressure, moisture may diffuse into a component and cause failure mechanisms similar to those found under THB, but at a faster rate. The equipment used to implement temperature-humidity-pressure-bias (THPB) testing is often called a highly accelerated stress tester (HAST).

The military has imposed a thermal shock requirement upon electronic equipment, as specified in paragraph 3.1 of MIL-STD-883C, Method 1011.9. The test standard does not require real-time testing of the device or even biasing during the temperature cycling. Typical prior-art thermal-shock chambers used to apply the standard mechanically move samples between hot and cold chambers, for example, by an elevator. Not only are such apparatus bulky, further their mechanical movement complicates the cabling required for the electrical and optical signals to and from device under in situ testing.

SUMMARY OF THE INVENTION

The invention may be summarized as accelerated testing using the additional parameter of thermal shock or fast temperature cycling. In order to achieve rapid thermal cycling within an ambient of elevated temperature and possibly humidity and pressure, the fast temperature cycling is achieved by pumping heat from the tested device at elevated temperature by such means as a thermoelectric cooler so as to cool the device.

DETAILED DESCRIPTION OF THE PREFERRED EMBODIMENT

Figure 1:
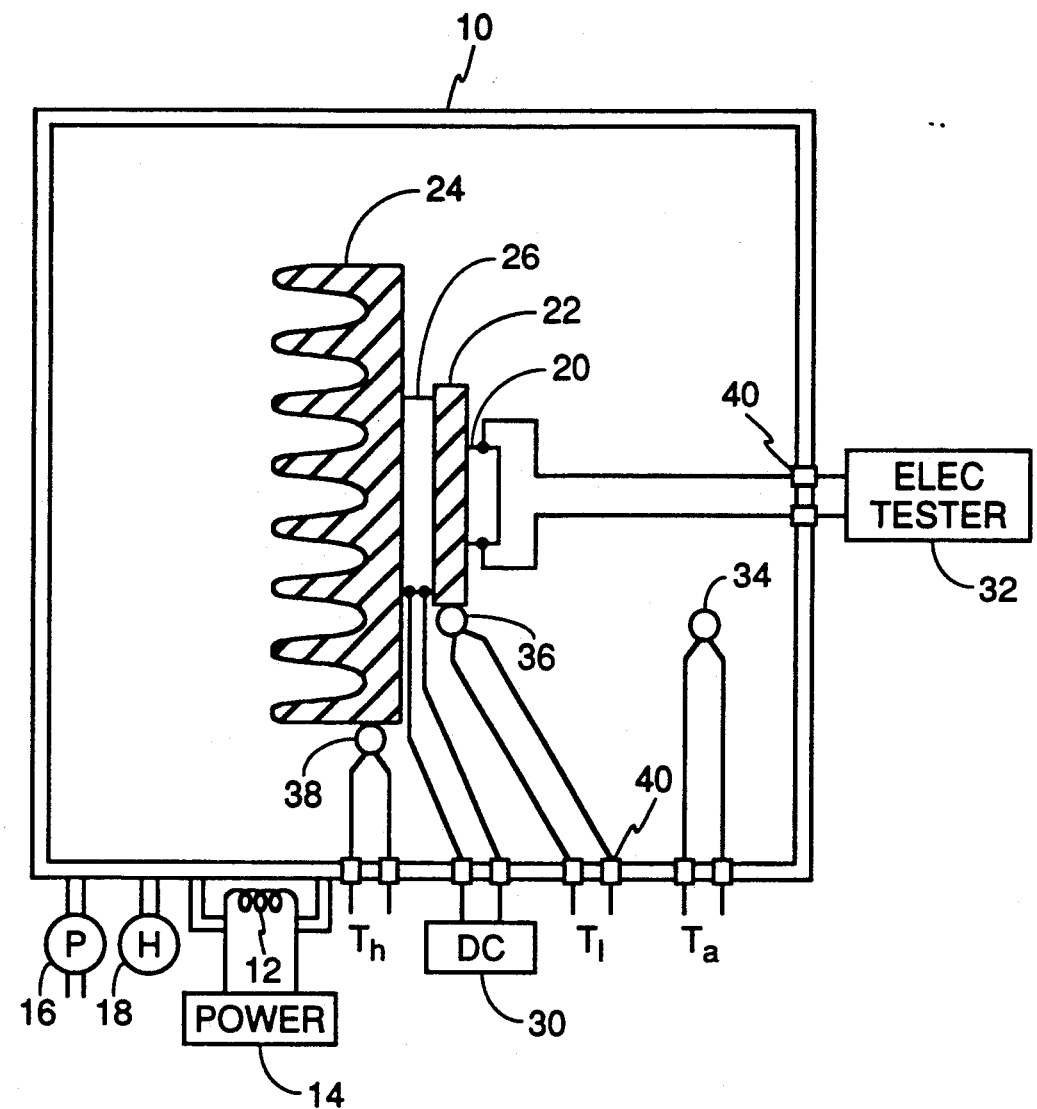
FIG. 1 is a schematic diagram of an embodiment of the invention, including a testing chamber.

An embodiment of the environmental test chamber of the invention is illustrated in FIG. 1. It conforms in most parts to a HAST (highly accelerated stress tester), such as Model 364 available from Expresstest of Sunnyvale, Calif. It includes a thermally insulated pressure vessel 10. A heater, such as a resistance blanket heater 12 surrounds the outer diameter of the chamber 10 and is selectively controlled by a power supply 14, which regulates the temperature within the vessel 10. Many other types of heaters are possible, including internal resistive heaters and steam sources, among other. In the experimental embodiment, a resistive thermal detector measured the temperature according to a temperature-dependent resistance. Below the boiling point of water, in the variable humidity mode, the pressure within the vessel 10 is controlled by pressurized air. However, at temperatures above the boiling point of water, the vapor pressure of the steam controls the pressure. Both of these effects will be functionally represented by a pump 16 controlling the pressure within the vessel 10 although other control mechanisms such as a directly controlled pump are possible. A humidity generator 18 generates a regulated amount of humidity within the vessel 10 and may, for example, be a steam generator which operates by resistively heating a pan of water to a temperature determined by a wet-bulb thermometer to the point that some of the water vaporizes into steam or humidity.

In this embodiment of the invention, a device under test 20 is thermally sunk to a primary heat sink 22. The primary heat sink 22 is often referred to as the load because the temperature of the primary heat sink 22 can be controlled more deterministically than that of the smaller device under test 20. A secondary, larger heat sink 24 is thermally coupled to the primary sink 20 by a heat pump 26. It preferably has a finned structure on its back in order to efficiently radiate heat. The heat sinks are typically large metal blocks. In an experimental embodiment, the primary heat sink 22 was copper, and the secondary one 24 was aluminum. As is typical in accelerated testing, the device under test 20 is detachably mounted to the primary heat sink 22. Because in the invention the temperature of the primary heat sink 22 differs from the ambient temperature within the vessel 10, it may be necessary to thermally insulate the device 20 from the vessel ambient while assuring its thermal coupling to the primary heat sink 22.

The heat pump 26 selectively pumps heat between the two heat sinks 22 and 24. A preferred type of heat pump 26 is a thermoelectric heat pump, commonly called a thermoelectric cooler. Such a thermoelectric device includes two dissimilar semi-metals in intimate contact, for example, bismuth telluride doped heavily to opposite semiconductivity types (n and p) on the two sides of its junction. Such a thermoelectric device is available as Model 04901-9L11-06A from Thermotrex of Waltham, Mass. A thermoelectric cooler operates according to the Peltier effect, that is, when a voltage is applied across the two sides of the junction, one side rises in temperature while the other side lowers. The two leads from the thermoelectric heat pump 26 are connected to a DC power supply 30. In one biasing polarity, the thermoelectric cooler 26 pumps heat from the primary heat sink 22, to which the device under test 20 is heat sunk, to the secondary heat sink 24; and, in the other biasing polarity, it pumps heat in the opposite direction from the secondary heat sink 24 to the primary heat sink 22. The heat is pumped regardless of which heat sink 22 or 24 is the hotter, up to the maximum temperature difference $\Delta T$ of the thermoelectric cooler in the thermal configuration of the test setup. That is, the heat pump 26 can operate against the thermal gradient. In contrast, the usual types of heater or cooler, e.g., a resistive heater or a cooling fluid, conduct or convect heat from the warmer body to the cooler body. In practice, the thermoelectric cooler 26 is used only in the cooling the primary heat sink 22 because, in the heating phase, the primary heat sink 22 quickly and effectively absorbs heat from the large thermal ambient. When the DC power supply 30 does not apply DC power to the thermoelectric heat pump 26, no heat is pumped although thermal conduction is possible from the hotter source to the cooler source. Because thermoelectric devices have only fractional efficiency, they always generate some local heat, which needs to be accounted for in the thermal design.

Further instrumentation is required to monitor the thermal environment and to test the device 20 in situ. Multiple electrical or fiber optical leads connect the device under test 20 to an electronic tester 32 which can electrically stress the device during the time the electric heat pump is operating. One thermocouple 34 monitors the ambient temperature $T_a$ within the pressure vessel 10. A second thermocouple 36 measures the temperature $T_l$ of the usually lower-temperature primary heat sink 22, and thus closely monitors the temperature of the device under test 20. A third thermocouple 38 monitors the temperature $T_h$ of the usually hotter secondary heat sink 24. The leads from the device under test 20 and from the three thermocouples 34, 36, and 38 are connected through the walls of the pressure vessel 10 by electrical feedthroughs 40 provided in the commercially available vessel 10. An unillustrated thermocouple recording device monitors the three temperatures as a function of time, and this data may combined with the electrical data from the electrical tester 32.

Somewhat similar results could be obtained by changing the vessel temperature by means of the heater 12. However, the thermal mass of the vessel 10 is relatively large and necessitates long equilibration periods. By thermal mass is meant the total heat capacity of the respective heat sink, that is, the specific heat capacity integrated over the volume of the body. Furthermore, the heater 12 is designed only to heat the vessel 10 to an elevated temperature, and it does not directly cool the vessel 10. Thus, the cooling period is controlled by thermal radiation out of the vessel 10, which is minimized in usual vessel designs, a contrary result for fast thermal cycling.

The secondary heat sink 24 could be effectively heat sunk to a closely regulated temperature, for example, by water cooling coils wound around it. However, when the secondary heat sink 24 has a larger thermal mass than the primary heat sink 22, both heat sinks 22 and 24 may as a combination be effectively thermally isolated within the pressure vessel 10 and radiate only to the chamber ambient. That is, no cooling fluid is required. By effective thermal isolation is meant that the heat pump 26 provides more thermal transfer than occurs from the heat sinks 22 and 24 to the exterior of the pressure vessel 10 or from the primary heat sink 22 to the vessel ambient. In the experimental embodiment, the heat sinks 22 and 24 and the thermoelectric cooler 26 between them rested upon a steel shelf, which provided little thermal conductivity to the exterior of the chamber 10.

A single-stage thermoelectric cooler can generate a temperature difference across its junction of as much as 70° C. For example, if the test is operating at an ambient temperature $T_a$ of 50° C. and it is desired to cool the device under test to freezing ($T_1 = 0$° C.), a thermoelectric cooler 26 having a maximum temperature difference of 70° C. requires that the maximum temperature rise in the secondary heat sink 24 be no more than 10° C. One can also calculate the thermal resistance of the secondary heat sink 24 required to produce a temperature rise of no more than 10° C. The thermal resistance is defined as the temperature difference between the hot side of the cooler $T_h$ and the ambient temperature $T_a$ divided by the electrical power into the cooler 26. If the thermoelectric cooler 26 requires 20 W of electrical power, it must have a thermal resistance of 0.5° C./W. This calculation has ignored the inherent inefficiency of the thermoelectric cooler 26, and the resistive power generated needs to be included.

Figure 2:
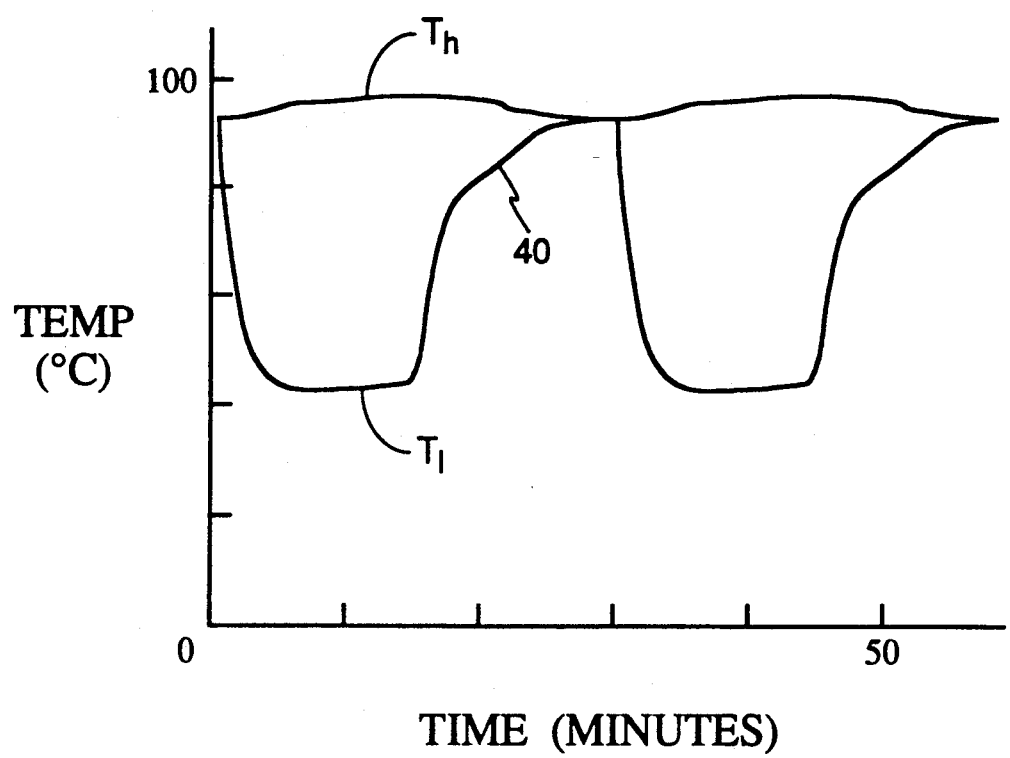
FIG. 2 is a plot of temperature cycling using the invention.

The invention was tested using a thermoelectric cooler providing a temperature difference $\Delta T$ of 50° C. The ambient temperature $T_a$ was set to 85° C., the relative humidity to 85%, and the vessel pressure to 45 psi (310,000 pa). In FIG. 2 are plotted the temperature $T_1$ of the primary heat sink 22 and the temperature $T_h$ of the secondary heat sink 24. The thermoelectric cooler 26 was powered in the cool-down portion only by 5A from the DC power supply 30. Two cycles of the testing were completed in 50 minutes. The temperature of the primary heat sink 22 was cycled from 85° C. down to 45° C. while the temperature of the secondary heat sink 24 varied only over 10° C. The plot for the primary heat sink 22 during the warm-up portion shows a kink 40 at around 81.5° C. This temperature corresponds to the dew point for the stated ambient temperature, pressure, and relative humidity. At the dew point, evaporation of the condensed humidity from the primary heat sink 22 produces a large amount of cooling. The kink 40 provides a further measurement of the ambient relative humidity.

The invention can be used to meet the speed requirement of the military standard for thermal shock defined in MIL-STD-883C, Method 1011.9. The standard requires that the equipment must cycle in 10 seconds and the device must reach equilibrium temperature in 5 minutes and remain at this dwell temperature for 2 minutes. Thermoelectric heat pumps have almost instantaneous cycle time, and the time for the device to reach the dwell temperature was measured to be under three minutes. The invention permits much easier in situ electrical testing since electrical and optical links remain stationary.

It is of course anticipated that the entire test procedure be performed under computer control, including establishment and control of ambient conditions, temperature cycling, and data acquisition of both environmental and device data.

The highest allowable operating temperature is limited by the maximum temperature rating of the heat pump and of the test chamber. A multi-stage heat pump can increase the maximum temperature difference between the two heat sinks.

A thermoelectric heat pump has the advantage of no moving mechanical parts and only electrical connections penetrating the vessel wall. However, the invention can utilize other types of heat pumps.

Although the invention is particularly useful for in situ testing of electronic and opto-electronic devices within HAST chambers, the invention can be advantageously used for tests of different types of parts and for less stressful test environments.

What is claimed is:

1. A thermal testing apparatus comprising
   a thermally controlled test chamber;
   a first body located within said chamber and to which may be thermally sunk a device under test;
   a second body located within said chamber;
   a heat pump selectively pumping heat between said first and said second body; and
   temperature maintaining means for maintaining an ambient temperature within said test chamber to a first temperature, and wherein said heat pump cools said first body to a temperature below said first temperature.

2. A thermal testing apparatus as recited in claim 1, wherein said first and second body are in combination effectively thermally isolated within said chamber.

3. A thermal testing apparatus as recited in claim 1, wherein said first body is effectively thermally isolated from an ambient within said chamber.

4. A thermal testing apparatus as recited in claim 1, wherein said heat pump is a thermoelectric device.

5. A thermal testing apparatus as recited in claim 1, wherein said first body is a first heat sink of a first thermal mass on which said device is detachably mounted and said second body is a second heat sink of a second thermal mass larger than said first thermal mass.

6. A thermal testing apparatus comprsing
   a thermally controlled test chamber;
   a first body located within said chamber and to which may be thermally sunk a device under test;
   a second body located within said chamber:
   a heat pump selectively pumping heat between said first and said second body;
   a heater maintaining an elevated ambient temperature within said test chamber;
   a pressure source maintaining an elevated pressure within said chamber; and
   a humidity source maintaining a humidity level within said chamber.

7. A thermal testing apparatus as recited in claim 6, further comprising an electrical tester testing said device while said heat pump, heater, pressure source, and humidity source are being operated.

8. A thermal testing apparatus as recited in claim 6 wherein said heat pump is a thermoelectric device.

9. A method of testing a device comprising the steps of
   placing a device under test on a first body inside an enrironmentally controlled chamber;
   pumping heat from said first body to a second body within said chamber, whereby a temperature of said device is lowered; and
   elevating a temperature within said chamber to an ambient temperature, and wherein said pumping step operates periodically to reduce a temperature of said device from approximately said ambient temperature to a lower temperature.

10. A method as recited in claim 9, further comprising: maintaining a given humidity level within said chamber; and pressurizing said chamber to an elevated pressure.

11. A method as recited in claim 9 wherein said device is an electrical or opto-electronic device and further including electrically stressing said device during said pumping step.

12. A method as recited in claim 9, wherein said pumping step uses a thermoelectric cooler.

* * * * *